(12) United States Patent
Malhotra et al.

(10) Patent No.: US 11,745,137 B2
(45) Date of Patent: Sep. 5, 2023

(54) DIAMINE SOLVENT SYSTEM FOR $CO_2$ CAPTURE

(71) Applicant: Battelle Memorial Institute, Richland, WA (US)

(72) Inventors: Deepika Malhotra, Richland, WA (US); Phillip K. Koech, Richland, WA (US); David J. Heldebrant, Richland, WA (US); Vassiliki-Alexandra Glezakou, Richland, WA (US); Roger J. Rousseau, Richland, WA (US); Manh Thuong Nguyen, Richland, WA (US); Robert Perry, Richland, WA (US); Jordan P. Page, Richland, WA (US); David C. Cantu, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 94 days.

(21) Appl. No.: 17/584,597

(22) Filed: Jan. 26, 2022

(65) Prior Publication Data
US 2022/0143548 A1    May 12, 2022

Related U.S. Application Data

(63) Continuation of application No. 16/363,672, filed on Mar. 25, 2019, now Pat. No. 11,266,947.

(51) Int. Cl.
*B01D 53/14* (2006.01)
*B01D 53/78* (2006.01)
(Continued)

(52) U.S. Cl.
CPC ..... *B01D 53/1493* (2013.01); *B01D 53/1425* (2013.01); *B01D 53/1475* (2013.01);
(Continued)

(58) Field of Classification Search
None
See application file for complete search history.

(56) References Cited

U.S. PATENT DOCUMENTS 8,765,951 B2    7/2014    Blair et al.
2013/0011314 A1    1/2013    Porcheron et al.
(Continued)

FOREIGN PATENT DOCUMENTS

| JP | 2006167520 | 6/2006 |
|---|---|---|
| JP | 2017159288 | 9/2017 |
| KR | 10-2016-0101696 | 8/2016 |

OTHER PUBLICATIONS

Chowdhury et al., "Development of novel tertiary amine absorbents for $CO_2$ capture," *Energy Procedia* 1:1241-1248, Feb. 1, 2009.
(Continued)

*Primary Examiner* — Daniel Berns
(74) *Attorney, Agent, or Firm* — Klarquist Sparkman, LLP

(57) ABSTRACT

Disclosed herein is a method and system for $CO_2$ removal from a gas stream using a diamine solvent having a Formula I

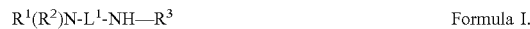
$R^1(R^2)N-L^1-NH-R^3$    Formula I.

With respect to Formula I, each of $R^1$ and $R^2$ independently is aliphatic, cycloaliphatic, or $R^1$ and $R^2$ together with the nitrogen to which they are attached, form a heterocyclyl ring; $L^1$ is aliphatic, cycloaliphatic, or $L^1$ and $R^1$ together with the nitrogen to which they are attached form a heterocyclyl ring; and $R^3$ is aliphatic, cycloaliphatic, cycloalkylalkyl, or alkoxyalkyl. And/or the compound may have a viscosity of less than 75 cP at a $CO_2$-loading of 40 mol % and at a temperature of 40° C.

1 Claim, 3 Drawing Sheets

(51) Int. Cl.
  *B01D 53/96* (2006.01)
  *C07D 295/13* (2006.01)
(52) U.S. Cl.
  CPC .... *C07D 295/13* (2013.01); *B01D 2252/2041* (2013.01); *B01D 2252/20426* (2013.01); *B01D 2252/20431* (2013.01); *B01D 2252/20452* (2013.01)

(56) References Cited

U.S. PATENT DOCUMENTS

| | | |
|---|---|---|
| 2014/0127103 A1 | 5/2014 | Yang et al. |
| 2016/0001220 A1 | 1/2016 | Higashii et al. |
| 2017/0246587 A1 | 8/2017 | Hong et al. |

OTHER PUBLICATIONS

Chowdhury et al., "$CO_2$ Capture by Tertiary Amine Absorbents: A Performance Comparison Study," *Industrial & Engineering Chemistry Research* 52:8323-8331, May 20, 2013.

Heldebrant et al., "Reversible zwitterionic liquids, the reaction of alkanol guanidines, alkanol amidines, and diamines with $CO_2$," *Green Chemistry* 12:713-721, Mar. 3, 2010.

Heldebrant et al., "Water-Lean Solvents for Post-Combustion $CO_2$ Capture: Fundamentals, Uncertainties, Opportunities, and Outlook," *Chemical Reviews* 117:9594-9624, Jun. 19, 2017.

International Search Report dated Nov. 2, 2020 from International Application No. PCT/US2020/023153.

Lepaumier et al., "New Amines for $CO_2$ Capture. 1. Mechanisms of Amine Degradation in the Presence of $CO_2$," *Industrial & Engineering Chemistry Research* 48:9061-9067, Sep. 28, 2009.

Martin et al., "New Amines for $CO_2$ Capture. IV. Degradation, Corrosion, and Quantitative Structure Property Relationship Model," *Industrial & Engineering Chemistry Research* 51:6283-6289, Apr. 8, 2012.

Singto et al., "Synthesis of new amines for enhanced carbon dioxide ($CO_2$) capture performance: The effect of chemical structure on equilibrium solubility, cyclic capacity, kinetics of absorption and regeneration, and heats of absorption and regeneration," *Separation and Purification Technology* 167:97-107, May 2, 2016.

Written Opinion dated Nov. 2, 2020 from International Application No. PCT/US2020/023153.

Yang et al., "Toward Intelligent $CO_2$ Capture Solvent Design through Experimental Solvent Development and Amine Synthesis," *Energy & Fuels* 30:7503-7510, Aug. 24, 2016.

DIAMINE SOLVENT SYSTEM FOR $CO_2$ CAPTURE

CROSS REFERENCE TO RELATED APPLICATION

This application claims the benefit of the earlier filing date of U.S. application Ser. No. 16/363,672, filed Mar. 25, 2019, which is incorporated herein by reference in its entirety.

ACKNOWLEDGMENT OF GOVERNMENT SUPPORT

This invention was made with Government support under Contract DE-AC05-76RL01830 awarded by the U.S. Department of Energy. The invention also was made under CRADA 363 between Battelle Memorial Institute and GE Global Research. The Government has certain rights in the invention.

FIELD

This disclosure concerns a method and system for removing $CO_2$ gas from a gas stream, using diamine compounds.

SUMMARY

Disclosed herein are embodiments of a method comprising contacting a gas stream comprising a first amount of $CO_2$ with a $CO_2$-lean solvent stream comprising a compound according to Formula I to form a treated gas stream comprising a second amount of $CO_2$ that is less than the first amount, and a $CO_2$-rich solvent stream, and heating the $CO_2$-rich solvent stream to form a $CO_2$ stream and regenerate the $CO_2$-lean solvent. The compound according to Formula I may have a structure:

$$R^1(R^2)N\text{-}L^1\text{-}NH\text{---}R^3 \qquad \text{Formula I.}$$

With respect to Formula I, each of $R^1$ and $R^2$ independently is aliphatic, cycloaliphatic, or $R^1$ and $R^2$ together with the nitrogen to which they are attached, form a heterocyclyl ring. $L^1$ is aliphatic, cycloaliphatic, or $L^1$ and $R^1$ together with the nitrogen to which they are attached form a heterocyclyl ring. And $R^3$ is aliphatic, cycloaliphatic, cycloalkyl-alkyl, or alkoxyalkyl. Additionally, the compound is not

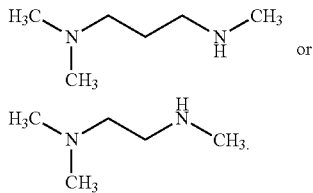

In some embodiments, the solvent consists essentially of the compound of Formula I.

In some embodiments, one or more of the following conditions may apply: i) at least one of $R^1$ and $R^2$ is branched alkyl or cycloalkyl; ii) $R^1$ forms a heterocyclyl with $L^1$; iii) $R^1$ and $R^2$ together with the nitrogen to which they are attached, forms a heterocyclyl ring; iv) at least one of $R^1$ and $R^2$ is not linear alkyl; or v) $R^3$ is alkoxyalkyl.

In some embodiments, the solvent does not contain an additional solvent, such as an affirmatively added solvent, including water. And in some embodiments, the solvent comprises less than 10 wt % water, the solvent typically absorbing such water from a $CO_2$-rich gas stream, such as an exhaust gas, at the same time as capturing $CO_2$.

Each of $R^1$ and $R^2$ independently may be $C_{1-6}$alkyl. But in certain embodiments, $R^1$ and $R^2$ together with the nitrogen to which they are attached form a heterocyclyl ring. In some embodiments, $L^1$ is $C_{2-4}$alkyl, but in other examples, $L^1$ and $R^1$ together with the nitrogen to which they are attached form a heterocyclyl ring. And/or in particular embodiments, $R^3$ is branched $C_{3-6}$alkyl or alkoxyalkyl.

The solvent may have a vapor pressure of less than 1 Torr at 40° C. and with a water content of less than 0.1 wt %, and/or a viscosity of less than 75 cP at a $CO_2$-loading of 40 mol % and at a temperature of 40° C.

Contacting the gas stream with $CO_2$-lean solvent may comprise contacting the gas stream at a first temperature of from 30° C. to 80° C. And/or heating the $CO_2$-rich solvent may comprise heating the $CO_2$-rich solvent to a second temperature of from 80° C. to 160° C. or more, such as from 100° C. to 160° C. Heating the $CO_2$-rich solvent may be performed at a pressure of from 1 atmosphere (atm) to 6 atms or more, such as from greater than 1 atm to 3 atms, or from 1.5 atms to 2 atms. And in some embodiments, the method further comprises cooling the regenerated $CO_2$-lean solvent to a temperature of from 30° C. to 60° C.

Also disclosed herein is a method comprising contacting a gas stream comprising a first amount of $CO_2$ with a solvent comprising a compound according to Formula I to form a treated gas stream comprising a second amount of $CO_2$ that is less than the first amount, and heating the $CO_2$-rich solvent stream to form a $CO_2$ stream and regenerate the solvent, thereby forming a $CO_2$-lean solvent stream, the solvent having a viscosity of less than 75 cP at a $CO_2$-loading of 40 mol % and at a temperature of 40° C. In some embodiments, the solvent does not comprise an additional solvent. And in some embodiments, the solvent has a vapor pressure of less than 1 Torr at 40° C. when measured with a water content of less than 0.1 wt %.

Also disclosed herein is a system, comprising an absorption unit comprising a gas inlet, a first solvent inlet and a first solvent outlet, a regeneration unit comprising a second solvent inlet fluidly coupled to the first solvent outlet, and a second solvent outlet fluidly coupled to the first solvent inlet, and a solvent comprising a compound according to Formula I. The system may further comprise a heat exchange unit fluidly coupled to the regeneration unit and the absorption unit such that the heat exchange unit facilitates transfer of heat energy from the solvent stream leaving the regeneration unit and to the solvent stream entering the regeneration unit.

The foregoing and other objects, features, and advantages of the invention will become more apparent from the following detailed description, which proceeds with reference to the accompanying figures.

DETAILED DESCRIPTION

I. Definitions

Figure 1:
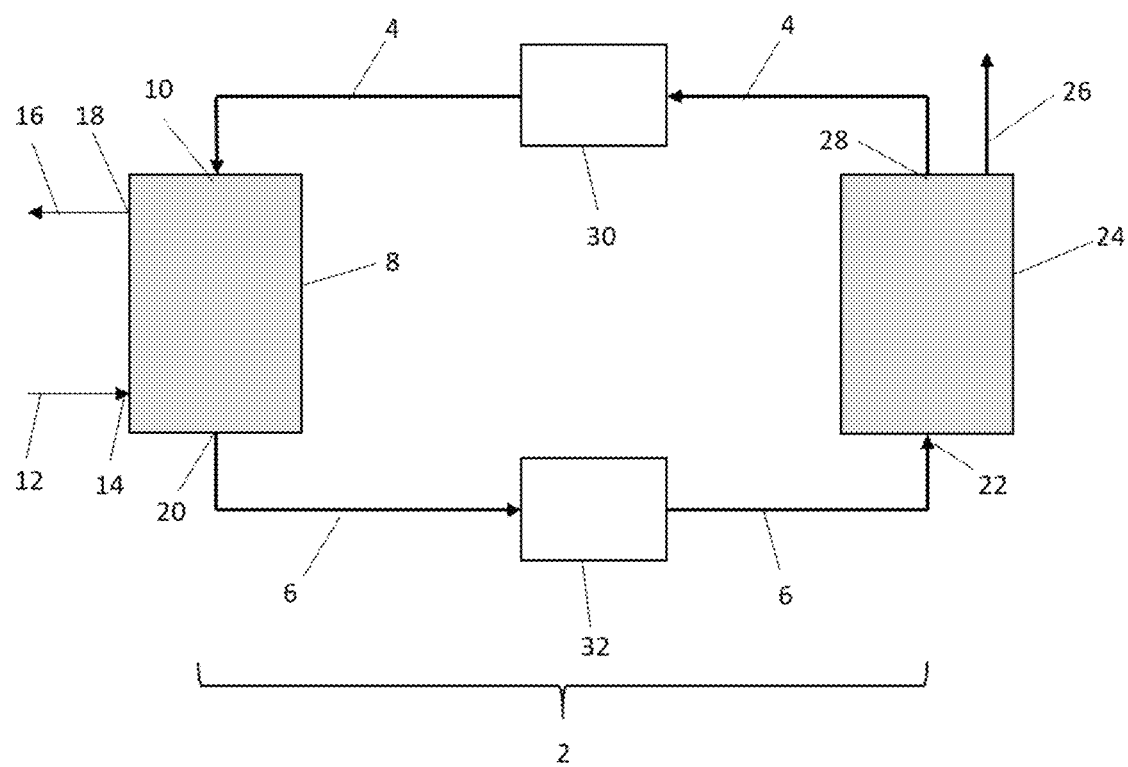
FIG. 1 is a schematic diagram illustrating an embodiment of a method for removing $CO_2$ from a gas stream using the disclosed compounds.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

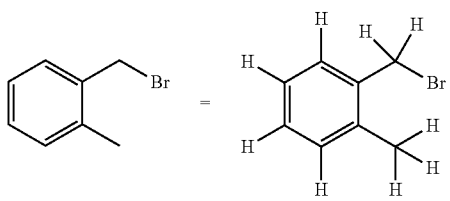

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms (C$_{1-25}$); for example, from one to fifteen (C$_{1-15}$), from one to ten (C$_{1-10}$), from one to six (C$_{1-6}$), or from one to four carbon atoms (C$_{1-4}$) for a saturated acyclic aliphatic group or moiety, from two to twenty-five carbon atoms (C$_{2-25}$); for example, from two to fifteen (C$_{2-15}$), from two to ten (C$_{2-10}$), from two to six (C$_{2-6}$), or from two to four carbon atoms (C$_{2-4}$) for an unsaturated acyclic aliphatic group or moiety, or from three to fifteen (C$_{3-15}$) from three to ten (C$_{3-10}$), from three to six (C$_{3-6}$), or from three to four (C$_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group).

"Alkoxy" refers to the group —OR, where R is a substituted or unsubstituted alkyl or a substituted or unsubstituted cycloalkyl group. In certain examples R is a C$_{1-6}$ alkyl group or a C$_{3-6}$ cycloalkyl group. Methoxy (—OCH$_3$) and ethoxy (—OCH$_2$CH$_3$) are exemplary alkoxy groups.

"Alkoxyalkyl" refers to the group -alkyl-OR or -cycloalkyl-OR, where R is a substituted or unsubstituted alkyl or a substituted or unsubstituted cycloalkyl group, as defined herein. —CH$_2$CH$_2$—O—CH$_2$CH$_3$ and —CH$_2$CH$_2$—O-cyclopropyl are exemplary alkoxyalkyl groups.

"Alkyl" refers to a saturated aliphatic hydrocarbyl group having from 1 to 25 (C$_{1-25}$) or more carbon atoms, more typically 1 to 10 (C$_{1-10}$) carbon atoms such as 1 to 6 (C$_{1-6}$) carbon atoms or 1 to 4 (C$_{1-4}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$—CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Cycloaliphatic" refers to a cyclic aliphatic group having a single ring (e.g., cyclohexyl), or multiple rings, such as in a fused, bridged or spirocyclic system, at least one of which is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, "Cycloalkylalkyl" refers to a cycloalkyl moiety as defined herein that is attached to the parent structure through an alkyl moiety. Cycloalkylalkyl moieties include, but are not limited to, cyclopropyl-methylene- or cyclopropyl-ethylene-.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon, or sulfur atom(s), preferably, N, O or S. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. In addition, annular nitrogen atoms can be optionally quaternized. Heterocyclyl includes heteroaryl moieties, and non-aromatic heterocyclyl moieties, also called heterocycloaliphatic moieties, which are heterocyclyl rings that are partially or fully saturated. Examples of heterocyclyl groups include, but are not limited to, pyridine, morpholine, piperazine, piperidine, homopiperidine, pyrrolidine, or thiomorpholine.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms.

"$CO_2$ capture" refers to $CO_2$ being taken up by the compound, such as by adsorption, absorption, forming a covalent bond, forming an ionic bond, or any combination thereof.

"$CO_2$-lean solvent" as used herein refers to a disclosed diamine solvent before it is exposed to a gas stream comprising $CO_2$. Typically, a $CO_2$-lean solvent comprises less than 25 mol % $CO_2$, and may comprise less than 20 mol %, than 15 mol % or less than 10 mol % $CO_2$.

"$CO_2$-rich solvent" as used herein refers to a disclosed diamine solvent after it has been exposed to a gas stream comprising $CO_2$ but before the solvent is regenerated. Typically, a $CO_2$-rich solvent comprises 20% or more $CO_2$, such as 25% or more, from 25 mol % to 60 mol %, or from 25 mol % to 50 mol %. A person of ordinary skill in the art understands that for a particular solvent, the $CO_2$-rich solvent has a greater $CO_2$ mol % than the corresponding $CO_2$-lean solvent. The difference between $CO_2$-rich and $CO_2$-lean for a particular solvent may be 5 mol % or more, such as at least 10 mol %, at least 15 mol %, at least 20 mol % or at least 25 mol %.

"Viscosity" is a measure of a fluid's resistance to flow and/or gradual deformation by shear stress or tensile stress. Viscosity is commonly expressed in centipoise (0.01 g/(cm·s), 0.001 N·s/m$^2$). As used herein, viscosity is determined at a temperature of 40° C. unless otherwise specified, and is measured using a substantially anhydrous compound, such as a compound having a water content of less than 0.1%, preferably from 10 to 100 ppm water.

"Vapor pressure" refers to the equilibrium pressure of a vapor above its liquid resulting from evaporation of the liquid at a particular temperature. As used herein, vapor pressure is determined at 40° C. unless otherwise specified. Typically, vapor pressure is measured in a closed container.

"Specific heat capacity" refers to the amount of heat energy required to raise the temperature of a unit mass of a substance by a given amount, typically 1 degree Celsius. For example, water has a specific heat capacity of 4.186 joule/gram° C.

II. Compounds

Disclosed herein are compounds suitable for capturing $CO_2$. In some embodiments, the compounds remain a liquid after exposure to $CO_2$ without the need for a co-solvent. Upon exposure to $CO_2$, the compounds may capture from greater than zero mol % $CO_2$, to 50 mol % or more, such as from greater than zero to 40 mol %, from 10 mol % to 40 mol %, or from 20 mol % to 40 mol %, while still remaining a liquid without a co-solvent. In some embodiments, the compounds have a viscosity of 75 cP or less, such as from 75 cP to greater than zero cP, or from 50 cP to greater than zero cP, at 40-50 mol % $CO_2$. And in certain embodiments, the compounds remain liquid, and/or have a viscosity of 50 cP or less, after exposure to $CO_2$ at a temperature of 40° C. Additionally, in some embodiments, the compounds have a low vapor pressure, such as a vapor pressure of less than 1 Torr at 40° C. before and after exposure to $CO_2$, such as from greater than zero to 1 Torr, from greater than zero to 0.75 Torr, greater than zero to 0.5 Torr, greater than zero to 0.1 Torr, or greater than zero to 0.01 Torr at 40° C.

In some embodiments, the compounds are diamine compounds and comprise a single hydrogen bond donor, typically —NH—, and a tertiary amine. The compounds do not comprise a primary amine. The compounds may also comprise 1, 2 or 3 additional hydrogen bond acceptors, such as a tertiary amine, an ether, or a combination thereof. In particular embodiments, the compounds comprise one tertiary amine and one secondary amine, and no additional nitrogen atoms. Such compounds may further comprise one or more ether moieties.

In certain embodiments, the compounds have a formula I $$R^1(R^2)N-L^1-NH-R^3 \qquad \text{Formula I.}$$

With respect to Formula I, each of $R^1$ and $R^2$ independently is aliphatic, preferably alkyl, such as $C_{1-6}$alkyl, $C_{1-4}$alkyl, $C_{1-3}$alkyl, or $C_{1-2}$alkyl; cycloaliphatic, preferably cycloalkyl, such as $C_{3-7}$cycloalkyl or $C_{3-4}$cycloalkyl, and may be cyclopropyl; or $R^1$ and $R^2$ together with the nitrogen to which they are attached, form a heterocyclyl ring, such as an non-aromatic heterocyclyl ring, preferably a 5- or 6-membered heterocyclyl ring and optionally comprising one or more additional heteroatoms, such as 1 or 2 heteroatoms selected from oxygen, nitrogen or sulfur, and/or optionally substituted with alkyl, such as $C_{1-4}$alkyl. Alternatively, $R^1$ may form a heterocyclyl moiety, with $L^1$, such as a non-aromatic heterocyclyl moiety, preferably a 5- or 6-membered heterocyclyl moiety. In such embodiments, $R^2$ is aliphatic, preferably alkyl, such as $C_{1-6}$alkyl, $C_{1-4}$alkyl, $C_{1-3}$alkyl, or $C_{1-2}$alkyl, or cycloalkyl, such as $C_{3-7}$cycloalkyl.

In some embodiments, each of $R^1$ and $R^2$ independently is linear alkyl or branched alkyl, such as $C_{1-6}$linear alkyl, or $C_{3-6}$branched alkyl. Exemplary linear alkyl moieties include, but are not limited to methyl, ethyl, n-propyl or n-butyl, and exemplary branched alkyl moieties include, but are not limited to, isopropyl, tert-butyl, iso-butyl, or sec-butyl. And $R^1$ and $R^2$ may be the same or different. In other embodiments, $R^1$ and $R^2$ together with the nitrogen to which they are attached form a non-aromatic heterocyclyl moiety, such as morpholine, thiomorpholine, piperidine, pyrrolidine, or piperazine, optionally substituted with $C_{1-4}$alkyl, typically, methyl, ethyl, isopropyl, or tert-butyl.

$L^1$ is aliphatic, preferably alkyl, such as $C_{2-4}$alkyl or $C_{2-3}$alkyl; cycloaliphatic, preferably cycloalkyl, such as $C_{5-7}$cycloalkyl; or $L^1$ and $R^1$ together with the nitrogen to which they are attached form a non-aromatic heterocyclyl ring, such as a 5-, 6-, or 7-membered heterocyclyl, optionally comprising one or more additional heteroatoms, such as 1 or 2 heteroatoms selected from oxygen, nitrogen or sulfur. In some embodiments, $L^1$ is $-CH_2CH_2-$ or $-CH_2CH_2CH_2-$, but in other embodiments, $L^1$ and $R^1$ together with the nitrogen to which they are attached, form a 5- or 6-membered non-aromatic heterocyclyl ring, such as a piperidine or pyrrolidine ring. In some such embodiments, $R^2$ is $C_{1-6}$alkyl, such as $C_{1-4}$alkyl, $C_{1-3}$alkyl, or $C_{1-2}$alkyl, preferably methyl or ethyl.

$R^3$ is aliphatic, cycloaliphatic, cycloalkylalkyl or alkoxyalkyl. In some embodiments, $R^3$ is alkyl, such as $C_{1-6}$alkyl, $C_{1-4}$alkyl, $C_{1-3}$alkyl, or $C_{1-2}$alkyl; cycloalkyl, such as $C_{3-7}$cycloalkyl or $C_{3-4}$cycloalkyl; cycloalkylalkyl, such as $-CH_2$cycloalkyl; or alkoxyalkyl, such as $C_{1-6}$alkyl, $C_{1-4}$alkyl, $C_{1-3}$alkyl, or $C_{1-2}$alkyl substituted $C_{1-4}$alkoxy, $C_{1-2}$alkoxy, or $C_{3-6}$cycloalkyl. $R^3$ may be linear or branched alkyl, and may be a linear $C_{1-6}$alkyl, $C_{1-4}$alkyl, $C_{1-3}$alkyl, or $C_{1-2}$alkyl or a branched $C_{3-6}$alkyl, $C_{3-4}$alkyl, or $C_3$alkyl. Exemplary linear and branched alkyl moieties include, but are not limited to, methyl, ethyl, n-propyl, or n-butyl, and isopropyl, isopropyl, tert-butyl, iso-butyl, or sec-butyl. In some embodiments, $R^3$ is unsubstituted, but in other embodiments, $R^3$ is substituted, and may be substituted with alkoxy, such as $C_{1-4}$alkoxy, or $C_{1-2}$alkoxy. Exemplary alkoxy substituents include, but are not limited to, methoxy, ethoxy, propoxy, isopropoxy or cycloalkoxy, such as cyclopropoxy.

In some embodiments, the compound is not

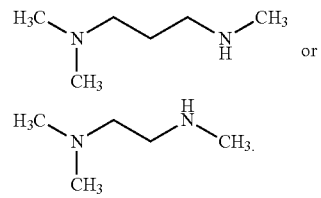

And in some embodiments, at least one of the following conditions applies:

i) at least one of $R^1$ and $R^2$ is branched alkyl or cycloalkyl;
ii) $R^1$ forms a heterocyclyl with $L^1$;
iii) $R^1$ and $R^2$ together with the nitrogen to which they are attached, forms a heterocyclyl ring;
iv) at least one of $R^1$ and $R^2$ is not linear alkyl;
v) $R^3$ is alkoxyalkyl.

And in particular embodiments, one or more of conditions i) to iv) applies.

Exemplary compounds within the scope of Formula I include:

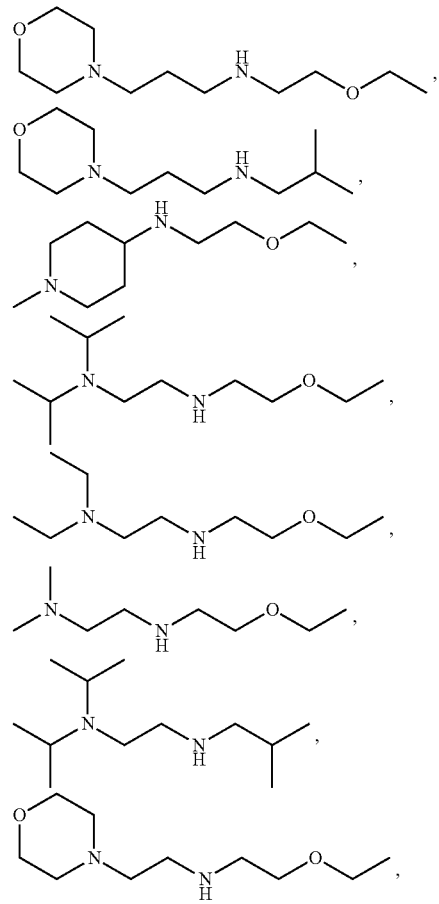

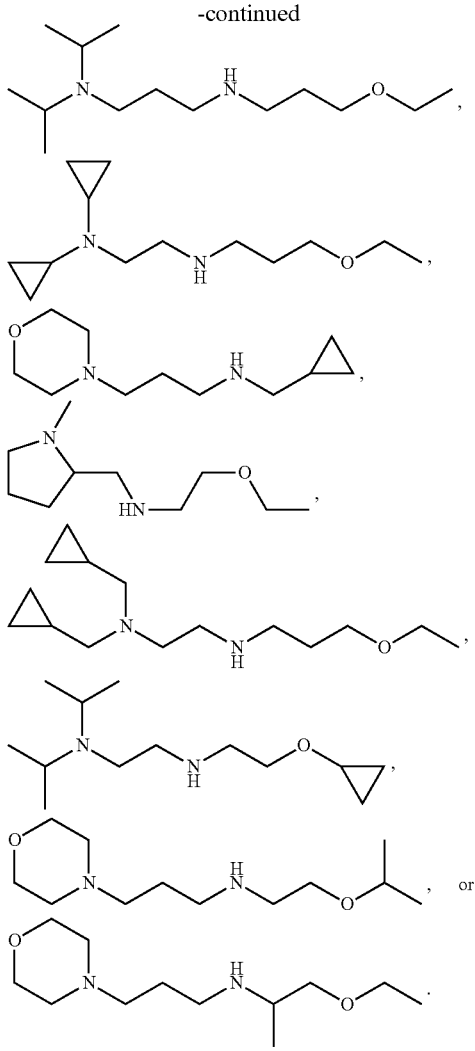

In particular embodiments, the compound is

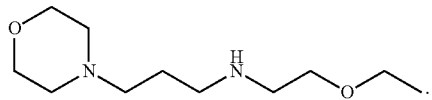

Without being bound to a particular theory, when a compound disclosed herein is exposed to $CO_2$ it may exist in an equilibrium between Formulas II, III and IV, as shown below.

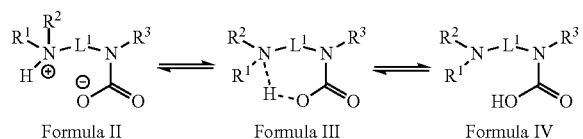

A person of ordinary skill in the art will understand that Formula II illustrates a zwitterionic state, while Formula IV illustrates the carbamic acid, and Formula III provides a potential intermediate state illustrating intramolecular bonding between the carbamate and the tertiary amine through the hydrogen. In some embodiments, when exposed to $CO_2$, the disclosed compounds form an equilibrium that comprises 50% or less of the zwitterionic form. The intramolecular H-bonding may shift the equilibrium toward a neutral form from the acid/base form. This in turn may reduce intermolecular bonding, which may help reduce the viscosity of the liquid, as the molecules can move more freely relative to each other. Additionally, limiting the compounds to a single hydrogen bond donor, such as a single secondary amine, also helps reduce the viscosity of the compound/$CO_2$ complex by reducing the intermolecular bonding between molecules.

Promoting intramolecular over intermolecular bonding may help reduce the viscosity of the compounds, but it also typically leads to compounds having a higher vapor pressures. This also may be due to the reduced bonding between the molecules, as the energy required for a molecule to enter the gaseous phase is reduced.

Surprisingly, the compounds disclosed herein have both a low viscosity when complexed with $CO_2$, and a low vapor pressure as discussed herein. In some embodiments, the vapor pressure is less than 1 Torr at 40° C. For comparison, $N^1,N^1$-dimethylethylene diamine has a literature vapor pressure of about 18 Torr (0.35 psi) at 20° C., and $N^1,N^1,N^2$-trimethylethylene diamine has a literature vapor pressure of about 17.8 Torr at 25° C. A person of ordinary skill in the art understands that vapor pressure typically increases Without being bound to a particular theory, the combination of the low viscosity and low vapor pressure may be due to the branched and/or cyclic moiety on the tertiary amine, and/or the ether moiety on the secondary amine. For example, when $N^1,N^1,N^3$-trimethylpropane-1,3-diamine has a $CO_2$ loading of 40 mol % or more, the viscosity at 40° C. is over 500 cP, when determined by the method disclosed herein, whereas when $N^1$-(2-ethoxyethyl)-$N^2,N^2$-diisopropylethane-1,2-diamine has a $CO_2$ loading of 40 mol % or more, its viscosity at 40° C. is less than 50 cP.

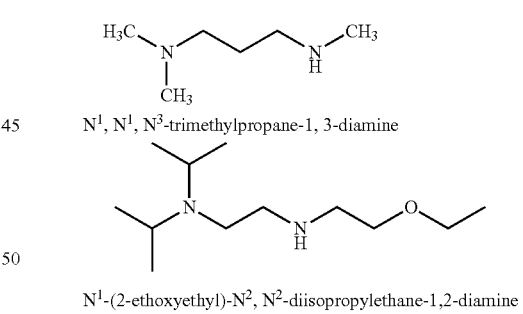

III. Synthesis

Disclosed compounds can be prepared as exemplified below, as illustrated for specific compounds in the examples, and as will be understood by a person of ordinary skill in the art or organic synthesis.

With respect to the following exemplary reaction schemes, $R^1$, $R^2$, $R^3$ and $L^1$ are as defined herein, and $R^4$ is aliphatic, preferably alkyl, such as $C_{1-5}$alkyl, $C_{1-4}$alkyl, $C_{1-3}$alkyl, or $C_{1-2}$alkyl; cycloaliphatic, preferably cycloalkyl, such as $C_{3-7}$cycloalkyl or $C_{3-4}$cycloalkyl; or cycloalkylalkyl; or alkoxyalkyl, such that $R^4$ and the carbon to which it is attached together form $R^3$ as defined herein.

An exemplary synthesis may include the following first reaction step according to Scheme 1.

Scheme 1

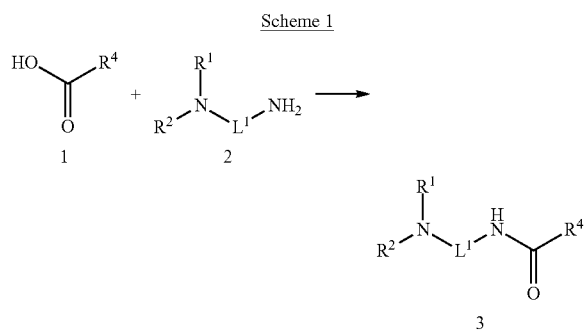

Acid 1 activated by a suitable activating agent in a suitable solvent and treated with amine 2 to form amide 3. The activating agent may be any agent suitable to facilitate acid 1 coupling to amine 2. Suitable activating agents include, but are not limited to, boric acid; a carbodiimide reagent, such as 1-ethyl-3-(3-dimethylaminopropyl)carbodiimide (EDC), or N,N'-dicyclohexylcarbodiimide (DCC), optionally in combination with hydroxybenzotriazole (HOBT); bis(2-oxo-3-oxazolidinyl)phosphinic chloride (BOP—Cl); thionyl chloride; mesyl chloride; tosyl chloride; or a combination thereof. Suitable solvents include, but are not limited to, aprotic solvents such as toluene, chlorinated solvents, such as chloroform or dichloromethane, dimethylformamide (DMF), tetrahydrofuran (THF), or a combination thereof. In some embodiments, the reaction may proceed with removal of water, such as by a drying agent or azeotropic water removal.

A second reaction step in the exemplary synthesis is provided below according to Scheme 2.

Scheme 2

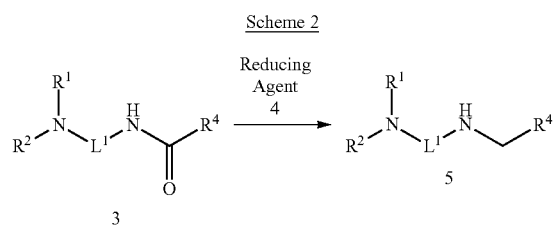

Amine 3 is treated with reducing agent 4 to form diamine 5. Reducing agent 4 can be any suitable reducing agent, such as lithium aluminum hydride, borane-dimethylsulfide, borane-THF, or lithium borohydride. And the reaction may be performed in a suitable solvent, such as THF, methanol, ether, or a combination thereof. And the reaction maybe performed at a temperature suitable to facilitate the reaction, such as from room temperature to reflux of the solvent.

Alternatively, the disclosed compounds may be made by the synthesis illustrated by Scheme 3.

Scheme 3

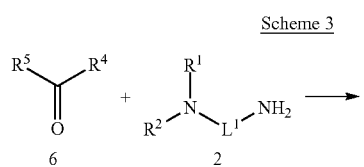

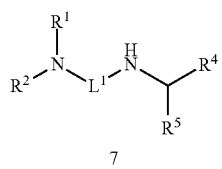

With respect to Scheme 3, $R^5$ is H or alkyl, such as $C_{1-6}$alkyl, $C_{1-4}$alkyl, ethyl, or methyl. Carbonyl compound 6 is treated with amine 2 and a reducing agent to form diamine 7. Suitable reducing agents are known to persons of ordinary skill in the art and may include, but are not limited to, borohydride reagents, such as sodium borohydride, sodium cyanoborohydride, sodium triacetoxyborohydride, or lithium borohydride, or catalytic reduction, such as by hydrogen with a palladium, nickel, ruthenium, or platinum catalyst, such as palladium on carbon. The reaction may be performed in one step, such as by reductive amination, or in two steps, where the amine and carbonyl compound are first allowed to react to form an imine, before being contacted by the reducing agent. A person of ordinary skill in the art will understand which solvent(s) are suitable for the particular reaction being performed, but suitable solvents may include alcohols, such as methanol, ethanol, or isopropanol, toluene, THF, acetonitrile, or a combination thereof.

Another exemplary synthesis suitable to produce the disclosed compounds is provided by Scheme 4.

Scheme 4

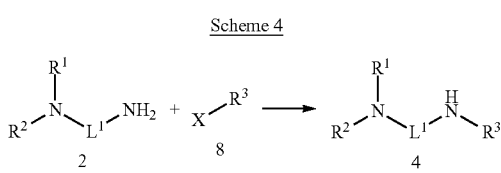

Amine 2 is treated with compound 8 to form compound 4. Typically, amine 2 is provided in excess, such as 2×, 3×, 4×, 5× or more excess with respect to compound 8, to facilitate the formation of compound 4, both to drive the reaction to completion and to limit formation of a tertiary amine. X is a suitable leaving group, such as, halogen, for example, bromo or chloro, methylate, or tosylate. The reaction may be performed neat, i.e., without an additional solvent, or alternatively, the reaction may be performed using a solvent. And the reaction may be performed in the presence or absence of an additionally added base. Suitable solvents include, but are not limited to, chlorinated solvents, such as chloroform or dichloromethane, toluene, acetonitrile, DMF, THF, pyridine or a combination thereof. And suitable bases include any base that will facilitate the reaction, such as a trialkylamine, for example, trimethylamine, pyridine, or an inorganic base, such as potassium carbonate. In some embodiments, the reaction mixture is contacted with an aqueous base to remove excess amine, and/or neutralize any salt of the product that may have formed. The reaction may be performed at a temperature suitable to facilitate the reaction, such as from 20° C. to 120° C. or more, or to reflux of the reactants and/or solvent, such as from 30° C. to 100° C., from 40° C. to 80° C., or from 40° C. to 60° C.

IV. Method and System for Using the Compounds

A. Overview

For the past century and a half, fossil fuels such as oil and coal have been used in energy production, such as electricity generation. Carbon dioxide, and other acidic gases that are a result of the combustion process, have been identified to be responsible for adverse environmental effects, and have been emitted on the gigaton scale globally. For example, according to the U.S. Department of Energy, a single subcritical coal-fired power plant of 550 MW size may produce over 6 million pounds of gas per hour, of which 1 million or more may be $CO_2$. The United States Department of Energy, in its efforts to maintain cost-effective energy production and reduce the environmental impact of fossil fuels, has set a target for next-generation $CO_2$ capture technology to have a total cost of $40/metric ton $CO_2$.

Various strategies have been developed for capturing acid gases, including carbon dioxide, from a gas stream using binding organic liquid (BOLs). However, these binding organic liquids have several issues that prevent them from achieving the DOE goal. These issues include 1) susceptibility to disproportionation and hydrolysis, therefore posing a huge challenge in terms of its recyclability and increased solvent replenishment costs; 2) significantly high $CO_2$ rich viscosity of the solvents requiring high recirculation rate leading to increased capital and operating expenses; and 3) the need for co-solvents leading to increased costs.

The compounds disclosed herein are readily synthesized, typically via only one or two reaction steps, and often from commercially available and inexpensive, starting materials. The compounds not only remain liquid when $CO_2$-rich, at typical operating temperatures, such as 40° C. or more, but they have a $CO_2$-laden viscosity sufficiently low that a co-solvent is not needed to facilitate efficient recirculation. Furthermore, the compounds are stable under conditions typically used for releasing the captured $CO_2$ and recycling liquid, such as heating to 100° C. or more, thereby reducing losses due to decomposition and extending the operating lifetime of the solvent.

Additionally, when exposed to a gas stream, such as during $CO_2$ capture as described herein, gaseous solvent molecules are lost with the treated gas stream. For solvents having higher vapor pressures, such as vapor pressures above 1 Torr at 40° C., these loses can amount to 1,000 pounds or more of solvent lost per hour for an industrial-scale application, such as a power station. Therefore, compounds having a low vapor pressure, such as a vapor pressure of less than 1 Torr at 40° C., such as the disclosed diamine compounds, are preferred because the low vapor pressure significantly reduces solvent loss due to exposure to the gas stream. In some embodiments, the disclosed compounds have a vapor pressure of less than 1 Torr at 40° C. before and after exposure to $CO_2$, such as from greater than zero to 1 Torr, from greater than zero to 0.75 Torr, greater than zero to 0.5 Torr, greater than zero to 0.1 Torr, or greater than zero to 0.01 Torr at 40° C.

Another advantage to the system disclosed herein is that the disclosed compounds are used without a co-solvent, i.e., without an additional solvent being affirmatively added to the disclosed compound(s). In current $CO_2$ removal systems, an amine is dissolved in a co-solvent, typically an aqueous solvent, to dissolve the $CO_2$ complex that forms. As discussed herein, amines typically form a solid, or very viscous, complex with $CO_2$, and the co-solvent is used to maintain a suitable viscosity such that the solvent system can flow to and from a regeneration unit. However, solvent regeneration typically involves heating the solvent to a temperature of 100° C. or more for organic solvents to release the $CO_2$, and typically is greater than 100° C., such as 120° C. or more for solvents comprising a water co-solvent. For solvents comprising a co-solvent, the co-solvent also has to be heated to the regeneration temperature. As previously mentioned, many current systems use an aqueous co-solvent. However, water has a high specific heat capacity of 4.186 joules/gram K. Organic liquids typically have lower specific heat capacities which means that they need less energy to heat the liquid by the same amount. For example, the specific heat capacities of ethylene diamine and trimethylamine are about 2.14 J/g K and 2.7 J/g K, respectively. And certain disclosed compounds have specific heat capacities of from 1.5 to 2.5 J/g K. Using the disclosed diamine solvents without a co-solvent results in a significant saving in the energy required to heat the solvent to the regeneration temperature.

B. Method for $CO_2$ Capture

Disclosed herein are embodiments of a method and system for removing $CO_2$ from a gas stream using a solvent comprising, consisting essentially of, or consisting of, one or more of the compounds disclosed herein. In some embodiments, the solvent does not include a co-solvent. However, combustion typically produces water as well as $CO_2$, and therefore the gas stream also may comprise water that is formed during combustion. Such water may be removed from the gas stream by the disclosed solvent, along with the $CO_2$, such that the solvent may comprise less than 10% water, such as from greater than zero to less than 10 wt %, from 2 wt % to 7 wt %, or about 5 wt % water. At least a portion of the water is removed from the solvent during solvent regeneration, such that the solvent may have a steady state water content of less than 10 wt %. A person of ordinary skill in the art understands that such water is not an affirmatively added and therefore is not a co-solvent. Also, the water is not present in sufficient quantities to be considered a co-solvent in the solvent system. Typically, when water is used as a co-solvent, the solvent system comprises 25%-30% or more water. Therefore, a solvent consisting essentially of one or more of the compounds disclosed herein may include the water that may be removed from a gas stream along with the $CO_2$, even though it does not include an affirmatively added co-solvent, such as an aqueous co-solvent.

The method may comprise contacting a gas stream comprising $CO_2$ with a $CO_2$-lean solvent, thereby facilitating capture of at least a portion of the $CO_2$ from the gas stream and forming a $CO_2$-rich solvent, and then releasing at least a portion of the captured $CO_2$ from the $CO_2$-rich solvent and regenerating the $CO_2$-lean solvent. The $CO_2$-lean solvent may comprise substantially zero mole percent (mol %) of $CO_2$ to less than 25 mol % $CO_2$, such as from 1 mol % to less than 25 mol % $CO_2$, from 5 mol % to less than 25 mol % $CO_2$, or from 10 mol % to 20 mol % $CO_2$. Additionally, or alternatively, the $CO_2$-rich solvent may comprise from 25 mol % to 60 mol % or more $CO_2$, such as from greater than 25 mol % to 50 mol %, or from 30 mol % to 45 mol % $CO_2$. As used herein, mole percent (mol %) refers to the number of moles of $CO_2$/the total number of moles of $CO_2$ and solvent×100%. A person of ordinary skill in the art understands that 50 mol % $CO_2$ refers to a 1:1 ratio between the number of moles of solvent molecules and the number of moles of $CO_2$ present in the solvent. In some embodiments, a $CO_2$ mol % difference between a $CO_2$-rich solvent and a $CO_2$-lean solvent is from greater than zero to 50 mol % $CO_2$ or more, such as from 5 mol % to 50 mol %, from 10 mol % to 40 mol %, from 5 mol % to 30 mol %, from 5 mol % to 20 mol %, or from 5 mol % to 15 mol %. In some embodiments, the $CO_2$ capture occurs under a first set of conditions and the $CO_2$ release and solvent regeneration occurs under a second set of conditions.

FIG. 1 provides schematic diagram of an exemplary process for removing at least a portion of the $CO_2$ from a gas stream. With respect to FIG. 1, solvent flow pathway 2 comprises $CO_2$-lean solvent stream 4 and $CO_2$-rich solvent stream 6.

$CO_2$-lean solvent stream 4 enters absorption unit 8 through inlet 10 and contacts $CO_2$-rich gas stream 12 that enters absorption unit 8 through gas inlet 14. Absorption unit 8 may be a column or tower, and/or may comprise materials and/or structures suitable to facilitate contact between the solvent and $CO_2$-rich gas stream 12, such as by providing an increased contact surface area. Absorption unit 8 may comprise mesh sheets, fibrous material, such as fiberglass, and/or packing materials, such as beads, balls, rings, saddle-shaped materials, tubes, or combinations thereof.

Typically, $CO_2$-lean solvent stream 4 contacts $CO_2$-rich gas stream 12 counter currently. Absorption unit 8 operates at a first temperature and a first pressure suitable to facilitate $CO_2$ capture by the solvent. The first temperature may be of from 25° C. to 100° C. or more, such as from 30° C. to 80° C. or from 40° C. to 60° C., and in some embodiments, $CO_2$ capture proceeds at about 40° C. And the first pressure typically is atmospheric pressure, such as 1 atm.

$CO_2$-rich gas stream 12 may comprise from greater than zero to 25 wt % or more, such as from 1 wt % to 20 wt %, from 1 wt % to 15 wt %, from 1 wt % to 10 wt % or from 1 wt % to 5 wt % $CO_2$. In certain embodiments, including embodiments comprising coal exhaust, such as from a coal-fired power plant, $CO_2$-rich gas stream 12 may comprise from 1 wt % to 15 wt % or more $CO_2$, such as from 5 wt % to 15 wt %, or from 10 wt % to 15 wt % $CO_2$. In other embodiments comprising gas exhaust, such as from a natural gas power plant, $CO_2$-rich gas stream 12 may comprise from 1 wt % to 10 wt % $CO_2$, such as from 1 wt % to 5 wt % $CO_2$, and may be about 4 wt % $CO_2$.

$CO_2$-lean solvent stream 4 captures at least a portion of the $CO_2$ present in $CO_2$-rich gas stream 12, thereby producing $CO_2$-lean gas stream 16 and $CO_2$-rich solvent stream 6. $CO_2$-lean gas stream 16 comprises a reduced amount of $CO_2$ compared to $CO_2$-rich gas stream 12, and exits absorption unit 8 through gas outlet 18. In some embodiments, $CO_2$-rich solvent stream 4 removes at least 60% of the $CO_2$ in the $CO_2$-rich gas stream 12, such as at least 70%, at least 80% or at least 90% of the $CO_2$ from the $CO_2$-rich gas stream. Therefore, $CO_2$-lean gas stream 16 comprises 40% or less $CO_2$ than the corresponding $CO_2$-rich gas stream after contact with solvent stream 4, such as 30% or less, 20% or less, or 10% or less $CO_2$.

$CO_2$-rich solvent stream 6 leaves absorption unit 8 through solvent outlet 20. Solvent outlet 20 is fluidly coupled to solvent inlet 22 in regeneration unit 24. In regeneration unit 24, $CO_2$-rich solvent stream 6 is heated to a second temperature suitable to facilitate release of at least a portion of the captured $CO_2$ thereby producing $CO_2$-lean solvent stream 2. $CO_2$ release and solvent regeneration typically proceeds at a second temperature greater that the first temperature. The second temperature may be a boiling point of the solvent, and/or may be from 100° C. to 160° C. or more, such as from 110° C. to 140° C. or from 120° C. to 140° C., and in some embodiments, release and regeneration proceeds at about 120° C. Solvent regeneration is performed at a second pressure suitable to facilitate $CO_2$ release and solvent regeneration. In some embodiments, the second pressure is from 1 atm to 6 atm or more, such as from greater than 1 at, to 3 atm, or from 1.5 atm to 3 atm. $CO_2$ that is released from the solvent exits the regeneration unit 24 as $CO_2$ stream 26.

$CO_2$-lean solvent stream 4 exits regeneration unit 24 through solvent outlet 28 which is fluidly coupled to solvent inlet 10 on absorption unit 8. Typically, as $CO_2$-lean solvent stream 4 leaves regeneration unit 24 it is at a temperature greater than the first temperature that is used in absorption unit 8. Therefore, pathway 2 may comprise cooling unit 30 that cools $CO_2$-lean solvent stream 4 such that the solvent stream enters absorption unit 10 at a temperature suitable to facilitate $CO_2$ capture, such as the first temperature.

In some embodiments, solvent pathway 2 further comprises a heating unit 32 that heats $CO_2$-rich solvent stream 6 prior to the solvent entering regeneration unit 24. Heating unit 32 may heat the solvent stream to a third temperature. The third temperature may be substantially the same as the second temperature, or greater, such that $CO_2$-rich solvent stream 6 enters regeneration unit 24 at substantially the second temperature. Alternatively, the third temperature may be an intermediate temperature between the first and second temperatures, such that the energy required to heat the $CO_2$-rich solvent stream 6 to the second temperature in regeneration unit 24 is reduced.

Figure 2:
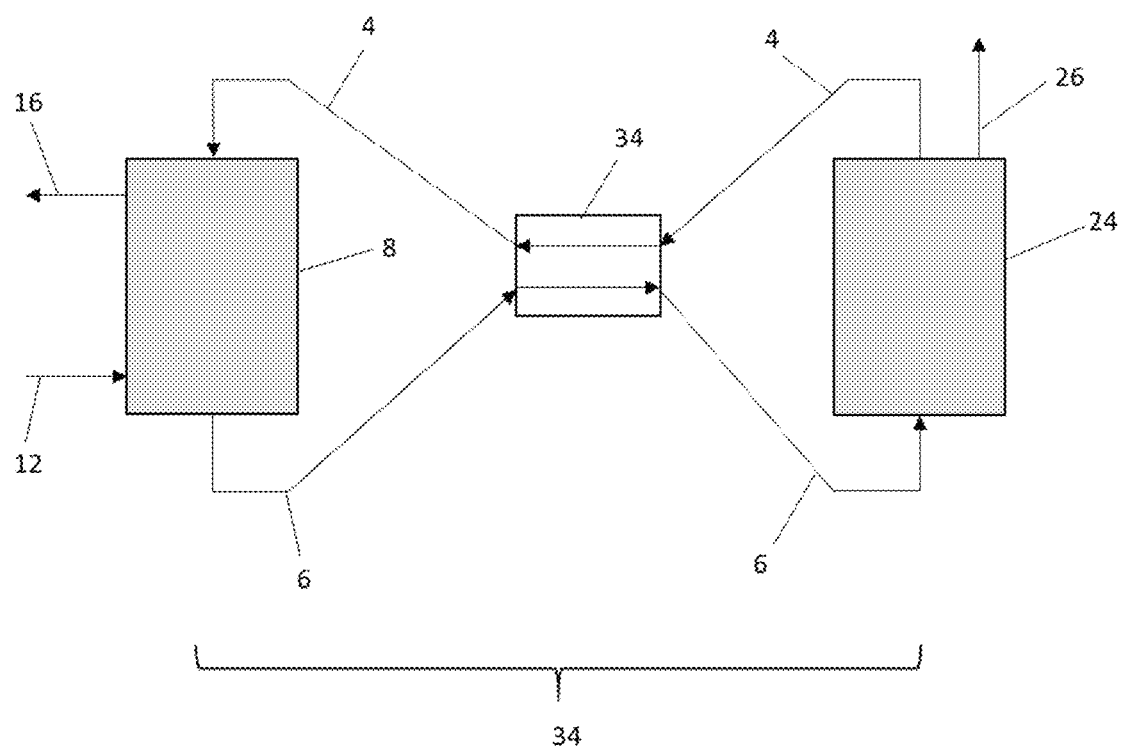
FIG. 2 is a schematic diagram illustrating an alternative embodiment of the method for removing $CO_2$ from a gas stream.

In certain embodiments, cooling unit 30 and heating unit 32 are combined into a heat exchanger unit 34. FIG. 2 provides an exemplary schematic diagram illustrating an alternative exemplary solvent flow pathway 34 comprising a heat exchanger. Solely in the interests of clarity, inlets 10, 14 and 22, and outlets 18, 20 and 28 are omitted from FIG. 2, but a person of ordinary skill in the art understands that they are still present in flow pathway 34. With respect to FIG. 2, heat exchanger 36 facilitates heat exchange between $CO_2$-lean solvent stream 4 and $CO_2$-rich solvent stream 6, such that $CO_2$-lean solvent stream 4 is cooled and $CO_2$-rich solvent stream 6 is heated. Typically, $CO_2$-rich solvent stream 6 enters heat exchanger 36 at about the first temperature, and leaves heat exchanger 36 at a temperature greater than the first temperature, and that may be at or less than the second temperature. Conversely, $CO_2$-lean solvent stream 4 enters heat exchanger 36 at a temperature of about the second temperature or less, but greater than the first temperature, and leaves at a temperature of from less than the second temperature to the first temperature.

In some embodiments, two or more systems disclosed herein are combined in series or in parallel. In certain embodiments, two or more systems are combined in parallel, such that a $CO_2$-rich gas stream is split between each of the disclosed systems to become $CO_2$-rich gas stream 12 for each system. In embodiments comprising two or more systems in series, $CO_2$-lean gas stream 16 that is output from a first system forms $CO_2$-rich gas stream 12 of a second system.

V. Examples

Example 1

Synthesis of
N-(2-ethoxyethyl)-3-morpholinopropan-1-amine (2)

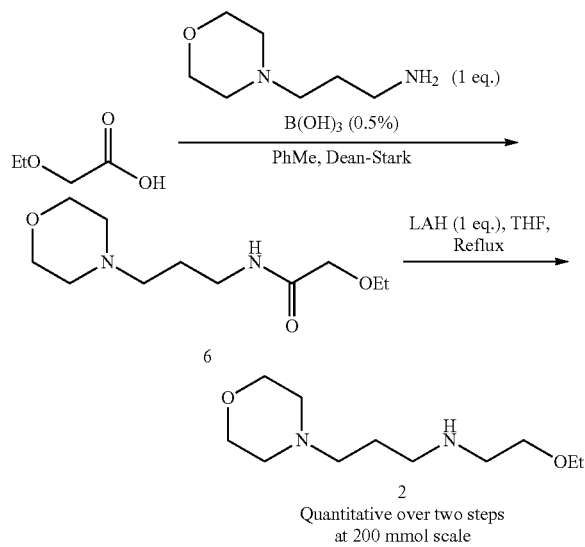

Quantitative over two steps
at 200 mmol scale

2-Ethoxy acetic acid (200 mmol), 3-morpholinopropane-1-amine (200 mmol) and 0.5% boric acid were heated to reflux in tolune with azeotropic removal of water. Heating continued until no more water was produced. The reaction mixture was cooled to room temperature, washed with aqueous base, dried and evaporated to leave compound 6.

6 was then treated with lithium aluminum hydride (200 mmol) in THF. The reaction was heated to reflux until TLC and/or NMR indicated that the reaction was substantially complete, then allowed to cool. Purification of compound 2, such as by distillation and/or chromatography, resulted in a substantially quantitative yield.

Example 2

Synthesis of
N-isobutyl-3-morpholinopropan-1-amine (8)

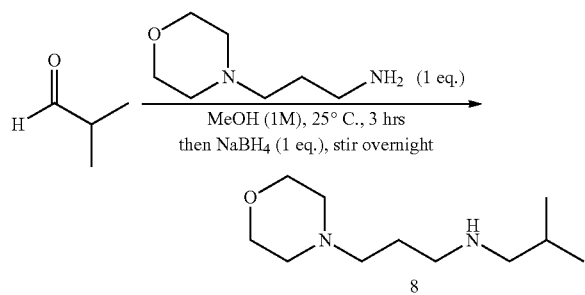

To a 500 mL three-necked round-bottom flask equipped with a magnetic stir bar, addition funnel, and ground glass stopper was added 60.0 mL (53.5 g, 370 mmol) 3-amino-propylmorpholine, and 300 mL methanol under nitrogen atmosphere. From the addition funnel, 40.0 mL (31.6 g, 438 mmol) isobutyrylaldehyde was added dropwise at room temperature over a period of 30 minutes, and the reaction was stirred for a further three hours, and the reaction was monitored by TLC plate each hour through the use of a UV lamp to see imine formation. The reaction was cooled to 0° C. and 15.44 g (408 mmol) of sodium borohydride was added in small portions until complete, and then the reaction was allowed to warm to room temperature overnight. A majority of methanol was removed by rotary evaporation, and the white slurry dissolved in 100 mL 10 M KOH (aq.), and the aqueous layer extracted (3×150 mL) dichloromethane. The combined organic layer was washed with 100 mL 10 M KOH and 250 mL distilled water, and then dried over MgSO$_4$, filtered, and evaporated. The product was distilled under reduced pressure (150 microns), the distillation apparatus equipped with a 17.5 cm Vigreux column and a short path equipped with a short Vigreux connection. The fractions at 85-88° C. was the product, and combined to yield 43.9 g (59% yield).

$^1$H NMR (CDCl$_3$, 500 MHz) δ: 0.88 (6H, d, J=6.5 Hz), 1.25 (1H, bs), 1.63-1.76 (3H, m), 2.36-2.41 (8H, m), 2.62 (2H, t, J=6.7 Hz), 3.69 (4H, t, J=4.5 Hz). $^{13}$C NMR (CDCl$_3$, 125.7 MHz): 67.0, 58.2, 57.5, 53.8, 48.8, 28.2, 26.8, 20.7 ppm.

Example 3

Alternative Synthesis of
N-(2-ethoxyethyl)-3-morpholinopropan-1-amine (2)

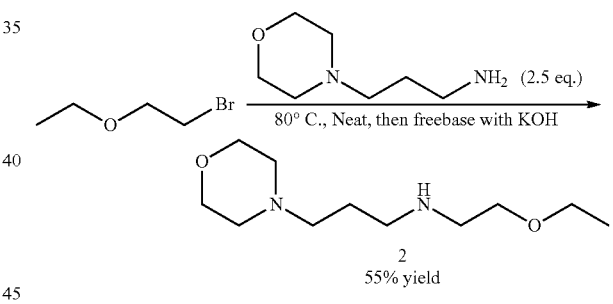

55% yield

To a 500 mL three-necked round-bottom flask equipped with a magnetic stir bar, addition funnel, an alcohol thermometer, and ground glass stopper was added 310 mL (307 g, 2.13 mol) 3-aminopropylmorpholine under nitrogen atmosphere. The amine was heated to an internal temperature of 80° C. and then 95.0 mL (116 g, 0.739 mol) of technical grade (90%) 2-bromoethyl ethyl ether was added dropwise to the neat amine. The internal temperature rose to approximately 110° C. and held steady until the complete addition. The reaction was allowed to slowly cool back to 80° C. and the reaction mixture was stirred overnight. The addition funnel was swapped with a short path distillation head, and the excess amine was distilled under reduced pressure. The gummy residue was poured warm into 250 mL chloroform chilled on ice, and washed with (2×250 mL) 10 M KOH (aq.) and (1×250 mL) distilled water. The organic layer was separated, and the combined aqueous washes were back extracted with 200 mL chloroform. The combined organic layer was dried over Na$_2$SO$_4$, filtered and evaporated. The product was distilled under reduced pressure (150 microns), the distillation apparatus equipped with a 17.5 cm Vigreux column and a short path equipped with a short Vigreux connection. The fractions at 100-105° C. was the product and combined to yield 88.7 g (55% yield).

$^1$H NMR (CDCl$_3$, 500 MHz) δ: 1.14 (3H, t, J=7.0 Hz), 1.47 (1H, bs), 1.59 (2H, p, J=7.2 Hz), 2.31-2.37 (6H, m), 2.61 (2H, t, J=7.2 Hz), 2.70 (2H, t, J=5.2 Hz), 3.39-3.48 (4H, m), 3.64 (4H, t, J=4.7 Hz). $^{13}$C NMR (CDCl$_3$, 125.7 MHz): 69.7, 66.8, 66.2, 57.2, 53.6, 49.4, 48.4, 26.7, 15.0 ppm. Mass Spec: C$_{11}$H$_{25}$N$_2$O$_2$$^+$ 217.3.

Example 4

PVT Cell for CO$_2$ Binding Organic Liquid (CO$_2$BOL) Viscosity

The viscosity of CO$_2$BOL derivatives was measured as a function of CO$_2$ loading using a custom designed flow cell designed to measure Vapor Liquid Equilibria (VLE) simultaneously with viscosity at a given temperature. The cell was made with stainless steel high vacuum components, totaling a 150 mL vapor volume. The fluid was circulated by a mechanical gear pump (Micropump GA series) and a custom wetted wall stainless steel contactor (Ø1.27×12.4 cm) inside the cell. Viscosity was measured in real time using a Cambridge Viscosity, SPC-372 sensor head (accuracy to +/−1.0% of full scale) and VISCOpro 2000 viscometer as the liquid sample was circulated inside the flow cell. Cell pressure was measured using temperature-controlled capacitance diaphragm gauges with an accuracy of 0.2% (Nor-Cal CDG-100 series). Cell temperature was controlled to within 0.1° C. by a large water bath to minimize temperature fluctuations. The operation range of the flow cell was 20° C.-100° C. and vacuum to 1 bar.

CO$_2$ absorption by the fluid was determined from temperature and pressure measurements and ideal gas equation of state, while liquid CO$_2$ loading was calculated from the mass balance.

In a typical experiment, a massed amount of fluid was loaded into the cell, and the cell was sealed, then the fluid was circulated and vacuumed to remove any physically dissolved gases in the fluid. Once steady state had been reached, the vacuum was shut off and the sample was allowed to reach its vapor pressure. Sequential metered injections of CO$_2$ gas (Oxarc 99.99%) from a calibrated volume were delivered into the flow cell using a Sievert-type apparatus. Continuous fluid circulation and an internal gas/liquid contactor provided mixing between CO$_2$ and the sample. Cell pressure was monitored visually, and viscosity, equilibrium pressure, and liquid CO$_2$ loading were recorded once the sample appeared to stop absorbing CO$_2$. Liquid CO$_2$ loading was calculated using the cell pressure change and the known cell volume. Additional CO$_2$ injections were made until a desired CO$_2$ loading was reached.

Accuracy of the flow cell was validated measuring VLE and viscosity data of a known solvent and compared with previously published viscosity and VLE data.

Figure 3:
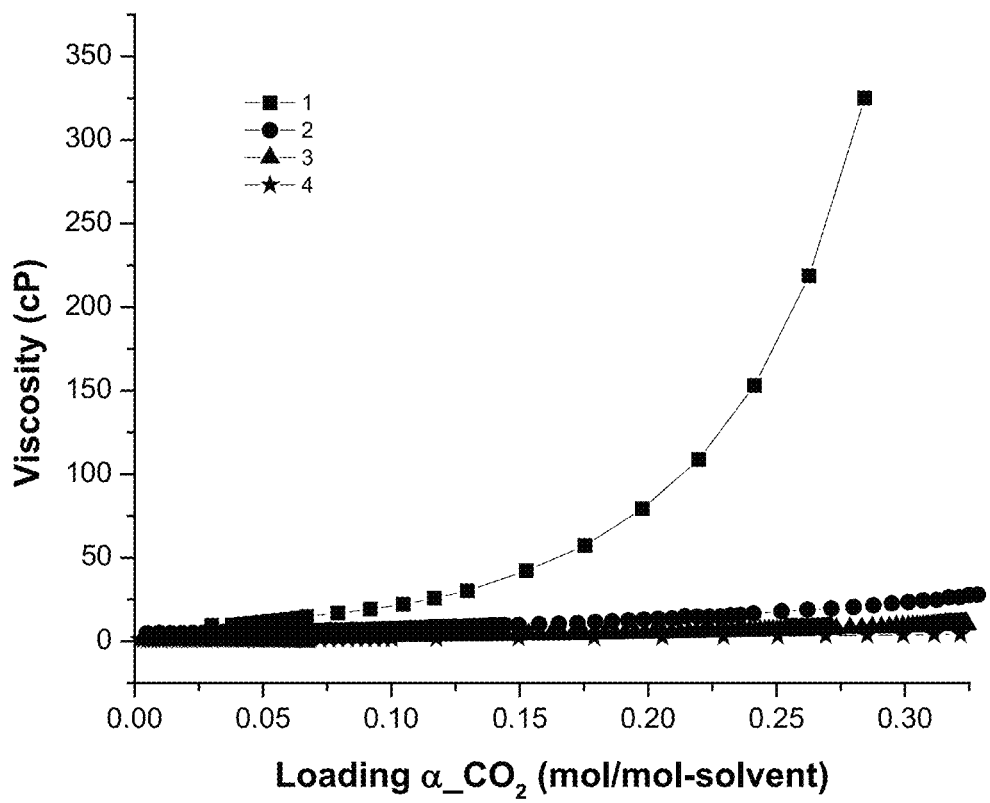
FIG. 3 is a graph of viscosity versus mol/mol-solvent (mol %) illustrating the viscosity of exemplary compounds at increasing $CO_2$ loading.
Figure 3:
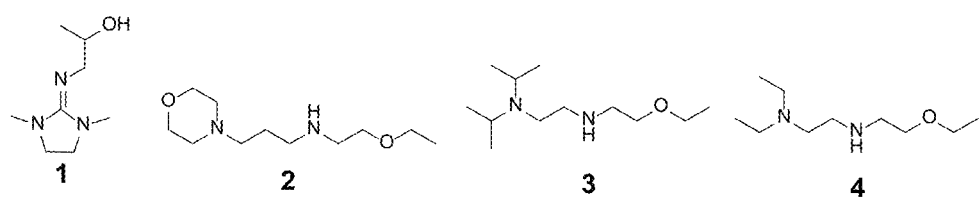

FIG. 3 provides results from viscosity test using three exemplary compounds of Formula I. As shown in FIG. 3, as the CO$_2$ loading increased to more than 30 mol % the viscosity of disclosed compounds 2, 3 and 4 remained below 50 cP. However, comparator compound 1 demonstrated a sharp increase in viscosity from about 15 mol % CO$_2$.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising:
   contacting a gas stream comprising a first amount of CO$_2$ with a CO$_2$-lean solvent stream comprising a compound according to Formula I at a first temperature of from 30° C. to 80° C., to form a treated gas stream comprising a second amount of CO$_2$ that is less than the first amount, and a CO$_2$-rich solvent stream;
   heating the CO$_2$-rich solvent stream to a second temperature of 80° C. to 160° C. to form a CO$_2$ stream and regenerate the CO$_2$-lean solvent; and
   cooling the regenerated CO$_2$-lean solvent to a temperature of from 30° C. to 60° C. wherein the compound has a structure according to Formula I

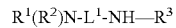
           Formula I each of R$^1$ and R$^2$ independently is alkyl, cycloalkyl, or R$^1$ and R$^2$ together with the nitrogen to which they are attached, form a heterocyclyl ring;
L$^1$ is C$_{2-4}$alkyl, or L$^1$ and R$^1$ together with the nitrogen to which they are attached form a 5- or 6-membered heterocyclyl ring; and
R$^3$ is branched C$_{3-6}$alkyl, or alkoxyalkyl;
wherein the compound has a vapor pressure of less than 1 Torr at 40° C. content of less than 0.1 wt %, and has a viscosity of less than 75 cP at a CO$_2$-loading of 40 mol % and at a temperature of 40° C.; and
at least one of the following conditions applies
i) at least one of R$^1$ and R$^2$ is branched alkyl or cycloalkyl;
ii) R$^1$ forms a heterocyclyl with L$^1$;
iii) R$^1$ and R$^2$ together with the nitrogen to which they are attached, forms a heterocyclyl ring;
iv) at least one of R$^1$ and R$^2$ is not linear alkyl; or
v) R$^3$ is alkoxyalkyl.

\* \* \* \* \*